United States Patent
Shimazu et al.

(10) Patent No.: US 7,931,793 B2
(45) Date of Patent: Apr. 26, 2011

(54) TIN OR TIN ALLOY ELECTROPLATING SOLUTION

(75) Inventors: Motoya Shimazu, Saitama (JP); Yasuo Ohta, Tokyo (JP)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 423 days.

(21) Appl. No.: 12/150,233

(22) Filed: Apr. 24, 2008

(65) Prior Publication Data

US 2008/0283406 A1      Nov. 20, 2008

(30) Foreign Application Priority Data

Apr. 24, 2007   (JP) ................. 2007-114798

(51) Int. Cl.
   *C25D 3/60*   (2006.01)
   *C25D 3/32*   (2006.01)
   *C23C 16/40*  (2006.01)

(52) U.S. Cl. ........ 205/304; 205/253; 205/302; 106/1.25
(58) Field of Classification Search .............. 205/253, 205/302, 304; 106/1.25
See application file for complete search history.

(56) References Cited

U.S. PATENT DOCUMENTS 2,739,972 A * 3/1956 Abbott et al. ................. 549/448

FOREIGN PATENT DOCUMENTS

JP          08269777 A  * 10/1996

* cited by examiner

*Primary Examiner* — Edna Wong
(74) *Attorney, Agent, or Firm* — John J. Piskorski

(57) ABSTRACT

An additive obtained from the reaction product obtained by reacting glutaraldehyde and at least one type of compound selected from hydrocarbon compounds containing a hydroxyl group, and at least one type of compound selected from amine compounds, as well as a tin or tin alloy plating solution containing this additive.

4 Claims, No Drawings

TIN OR TIN ALLOY ELECTROPLATING SOLUTION

The present invention relates to a tin or tin alloy electroplating solution and to an additive. In further detail, the present invention relates to a novel additive for an acidic-based electrolytic tin or tin alloy plating solution that is particularly preferable for use with barrel plating, and to a tin or tin alloy plating solution using this additive.

Tin and tin alloy plating is used in electronic components that require electrical connections, such as chip components, lead frames, print board circuits, and the like, because of the excellent connecting properties, low cost, electrical properties, and soldering properties.

Surface mounting chip components such as resistors and capacitors, and the like, which are used in surface mounting are generally tin plated on the electrodes using a barrel plating method in order to provide soldering properties to the electrodes. Problems are known with the barrel plating method where the chip components will congregate together, or in other words the chip components will adhere to one another. In order to prevent this congregation, a complexing agent is added to the tin plating solution and therefore the tin plating solution is slightly acidic (pH between 3 and 5) (for example see Japanese unexamined patent application 2001-24093). However, the complexing agents used in tin plating solutions are generally compounds which do not naturally decompose, and therefore are a burden on the environment unless appropriate waste water treatment is performed. Therefore, waste water treatment of the plating solution and the wash water which contain the complexing agent is complicated and expensive, so there is demand for a tin plating solution which does not contain a complexing agent.

Furthermore, strongly acidic tin plating solutions have been proposed such as those containing an aromatic aldehyde and a low-level aliphatic aldehyde in a tin plating solution that uses an alkanesulfonic acid (for example see Japanese unexamined patent application S61-223193), those using the reaction products of acetaldehyde or an aldol condensate of acetaldehyde and a compound selected from a group consisting of ammonia, non-cyclic ketones, aliphatic amines, aliphatic amides, aliphatic amino acids, and aliphatic hydrazine compounds (for example see Japanese unexamined patent application H2-232389), and those containing an aromatic aldehyde and an N-substituted unsaturated aliphatic amide compound (for example see Japanese unexamined patent application H4-83894). However, there are no products that are effective at preventing chip components from adhering together when using a barrel plating method.

An objective of the present invention is to provide an electrolytic tin or tin alloy plating solution and additive that can resolve the aforementioned problems, has little burden on the environment, does not require complicated waste water treatment, suppresses the chip components from adhering together when using a barrel plating method, and which can perform uniform tin or tin alloy plating.

As a result of diligent investigations to resolve the aforementioned problems, the present inventors have discovered that the aforementioned objectives can be achieved by using a compound obtained by reacting specific components in a tin or tin alloy plating solution, and have thus achieved the present invention. In other words, the present invention is an additive that provides a tin or tin alloy plating solution, comprising:

(1) a reaction product obtained by reacting glutaraldehyde and at least one type of compound selected from hydrocarbon compounds containing a hydroxyl group in the presence of an acid; and
(2) at least one type of compound selected from amine compounds.

Furthermore, the present invention is a tin or tin alloy electroplating solution that provides a plating solution comprising:
(1) stannous ion;
(2) acidic component;
(3) reaction product obtained by reacting at least one type of compound selected from amine compounds with the product obtained by reacting glutaraldehyde and at least one type of compound selected from hydrocarbon compounds containing a hydroxyl group in the presence of an acid; and
(4) a nonionic surfactant.

Furthermore, the present invention provides an additive for a tin or tin alloy electroplating solution, comprising the product obtained by reacting glutaraldehyde and at least one type of compound selected from hydrocarbon compounds containing a hydroxyl group in the presence of an acid and at least one type of compound selected from amine compounds.

Furthermore, the present invention is a manufacturing method of an additive for a tin or tin alloy electroplating solution that provides a manufacturing method for an additive comprising:
(1) a step of reacting glutaraldehyde and at least one type of compound selected from hydrocarbon compounds containing a hydroxyl group in the presence of an acid; and
(2) a step of adding at least one type of compound selected from amine compounds to the reaction solution.

The present invention also provides a manufacturing method for an acidic tin or tin alloy electroplating solution, wherein the aforementioned additive is added to an acidic solution containing stannous ion and an acid component.

Using the tin plating solution of the present invention can suppress the objects for plating from adhering together when barrel plating, and can provide a plating film which has excellent soldering properties without using a complexing agent which is a heavy burden on the environment and requires complicated waste water treatment. Furthermore, the aforementioned tin plating solution can be provided by using the additive for a tin plating solution of the present invention.

The present invention will be described below in detail. The tin plating solution of the present invention comprises the reaction product of the additive (A) shown below, stannous ions, an acid component, and optionally other metal ions, optionally a nonionic surfactant, and optionally an antioxidant.

The abbreviations used throughout this specification have the following meaning unless otherwise designated.
g=gram; mg=milligram; ° C.=degrees Celsius; min=minute; m=meter; cm=centimeter; L=liter; mL=milliliter; A=Ampere; $dm^2$=square decimeter. All numerical ranges are inclusive and may be combined in any order. The terms "plating solution" and "plating bath" used throughout this specification are used interchangeably and have the same meaning. The terms "alkane" and "alkanol" refer to straight chain or branched chain alkanes or alkanols. In this specification, the phrase "solution of a hydrocarbon compound containing a hydroxyl group" refers to mixtures of solvent and a hydrocarbon compound containing a hydroxyl group or to the hydrocarbon compound containing a hydroxyl group itself.

Additive (A) for the tin or tin alloy electroplating solution of the present invention is a composition that comprises the reaction product obtained by reacting glutaraldehyde and at least one type of compound selected from hydrocarbon compounds containing a hydroxyl group in the presence of an acid, and at least one type of compound selected from amine compounds.

Hydrocarbon compounds containing a hydroxyl group refers to hydrocarbon compounds which have one or more hydroxyl groups. Preferable hydrocarbon compounds containing a hydroxyl group are straight chain, branched, or cyclical substituted or unsubstituted compounds with between 1 and 10 carbons, more preferably between 1 and 6 carbons, and even more preferably between 1 and 3 carbons which have between 1 and 6 hydroxyl groups, more preferably with between 1 and 3 hydroxyl groups, and examples include monohydric or polyhydric alcohols and sugars, and the like. Specific examples of hydrocarbon compounds containing a hydroxyl group are monoalcohol compounds, glycol compounds, glycerin compounds, sugars, and sugar alcohols, and the like. Examples of monoalcohol compounds include methanol, ethanol, propanol, isopropanol, and phenol, and the like. Examples of glycol compounds include ethylene glycol, 1,3-propylene glycol, 1,2-propylene glycol, 1,2-butylene glycol, 1,3-butylene glycol, 1,4-butylene glycol, 1,2-isobutylene glycol, 1,3-isobutylene glycol, and the like. An example of a sugar is glucose, or the like. An example of a sugar alcohol is sorbitol, or the like. Preferable hydrocarbon compounds containing a hydroxyl group of the present invention are ethylene glycol, 1,2-propylene glycol, and 1,3-propylene glycol.

The reaction between the aforementioned hydrocarbon compound containing a hydroxyl group and glutaraldehyde, for instance, is performed as a result of mixing glutaraldehyde with at least one type of hydrocarbon compound containing a hydroxyl group in the presence of an acid. The reaction can be performed by adding and blending glutaraldehyde with a hydrocarbon compound containing a hydroxyl group in a solvent, or by blending without using a solvent. Furthermore, blending can be performed after diluting either one or both of the hydrocarbon compounds containing a hydroxyl group and the glutaraldehyde with a solvent. The solvent can be a polar solvent such as water or an alcohol such as methanol or ethanol, or the like. The glutaraldehyde is blended with an equivalent molar amount, or less than an equivalent molar amount of the hydrocarbon compound containing a hydroxyl group. The reaction time is preferably maintained between 0.5 hours and 3 hours by maintaining the solution temperature between 30° C. and 70° C.

The acid is provided to the reaction solution by adding an acidic component, and for instance, can be provided by adding an acidic component to the solution of a hydrocarbon compound containing a hydroxyl group, or by adding an acidic component to a mixture of glutaraldehyde and a hydrocarbon compound containing a hydroxyl group. Examples of the acidic component include sulfuric acid, hydrochloric acid, alkanesulfonic acid, and alkanolsulfonic acid, and the like.

Examples of the amine compound include ammonia, ethylenediamine, diethylenetriamine, n-propylamine, 1,2-propanediamine, 1,3-propanediamine, dimethylamine, hexamethylenetetramine, tetraethylenepentamine, triethanolamine, hexamethylenediamine, polyoxyalkylamine, polyoxyalkyldiamine, polyoxyalkyltriamine, and the like. A composition that contains a polyoxyalkylamine or a polyoxyalkyldiamine and the reaction products of glutaraldehyde and 1,2-propylene glycol or 1,3-propylene glycol is preferable. Particularly preferable amine compounds are those selected from the compounds expressed by Formula (I).

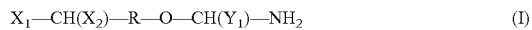

$X_1$—$CH(X_2)$—R—O—$CH(Y_1)$—$NH_2$ (I)

In the aforementioned formula, $X_1$ is a hydrogen atom or an amino group, $X_2$ is a hydrogen atom or a $C_1$-$C_3$ alkyl group, or an amino group, $Y_1$ is a hydrogen atom or a $C_1$-$C_3$ alkyl group, or an amino group, and R is a polyoxyalkyl group. For example, R is —O—$CH_2$—, O—$CH_2$—$CH_2$—, —O—CH($CH_3$)—, —O—($CH_2$)$_3$—, —O—CH($CH_3$)—$CH_2$— or —O—$CH_2$—CH($CH_3$)—.

The target Additive (A) can be obtained by adding at one time and mixing the amine compound selected above to the reaction solution of the glutaraldehyde and the hydrocarbon compound containing a hydroxyl group, in a quantity such that the solution obtained will be alkaline with a pH of 9 or higher, preferably between 9.5 and 12.0. Furthermore, the amount of amine compound added is preferably an equivalent to or higher than the molar amount of the glutaraldehyde for the case where a monoamine compound is used, and is preferably one half or more of an equivalent molar amount of the glutaraldehyde for the case where a diamine compound is used, and is preferably one third or more of an equivalent molar amount of the glutaraldehyde for the case where a triamine compound is used.

For instance, the specific method for manufacturing the additive (A) of the present invention is a method comprising:
(1) a step of preparing at least one type of hydrocarbon compound containing a hydroxyl group;
(2) a step of obtaining an acidic solution of a hydrocarbon compound containing a hydroxyl group by adding an acidic component to the aforementioned solution of a hydrocarbon compound containing a hydroxyl group, and then mixing for between 5 minutes and 15 minutes at a liquid temperature of between 30° C. and 70° C., preferably between 40° C. and 50° C.;
(3) a step of obtaining a reaction product's solution by adding an amount of glutaraldehyde no more than the equivalent molar amount of hydrocarbon containing a hydroxyl group in the acidic solution of hydrocarbon compound containing a hydroxyl group obtained, and then mixing at a solution temperature between 30° C. and 70° C., preferably between 40° C. and 50° C., for between 30 minutes and 3 hours, preferably between 45 minutes and 70 minutes;
(4) optionally, a step of bringing the liquid temperature of the reaction product solution to 40° C. or less, preferably between 20° C. and 25° C.;
(5) optionally, a step of adding a nonionic surfactant; and
(6) a step of adding to the solution that is obtained at least one type of amine compound in an amount no less than the equivalent molar amount (for the case of a monoamine compound) of glutaraldehyde.

Examples of the nonionic surfactant that can be used in step (5) include polyoxyethylene lauryl ether, polyethylene glycol, polyoxyethylene alkyl ether, polyoxyethylene polyoxypropylene glycol, polyoxyethylene nonylphenyl ether, polyoxyethylene polyoxypropylene alkylamine, and polyoxyethylene adducts of ethylenediamines, and the like, but polyoxyethylene monoalkyl ether or phenolethoxylate are preferable. These surfactants can be commercially procured, and can be purchased from ADEKA Corporation as a product named Adekatol™ PC-8. These nonionic surfactants may be used independently or as a mixture of two or more.

The amount of additive (A) of the present invention that is added to 1 L of the tin plating solution is an amount of additive (A) that contains between 0.5 and 50 g, preferably between 2 and 20 g of the reaction products of glutaraldehyde and a hydrocarbon compound containing a hydroxyl group. The reaction product's solution obtained can be added to the tin plating solution as is, or can be used after purifying by filtering or distilling, or the like.

Additive (A) of the present invention is thought to form additive reaction products which are useful in tin or tin alloy plating solutions because the amine compounds react with the reaction products of the glutaraldehyde and the hydrocarbon compound containing a hydroxyl group in the additive (A) by coming in contact with an acidic solution. If the reaction product of glutaraldehyde and at least one type of compound selected from hydrocarbon compounds containing a hydroxyl group and at least one type of compound selected from amine compounds are added individually to an acidic solution without mixing, the desired reaction will not occur and additive reaction products which are useful in a tin or tin alloy plating solution will not be formed. Theoretically, restricting is not preferable, but the reaction between at least one type of compound selected from amine compounds and the reaction products between glutaraldehyde and at least one type of compound selected from hydrocarbon compounds containing a hydroxyl group is thought to proceed when the additive (A) which is alkaline moves from being alkaline through the neutral region and becomes acidic, and is thought that the reaction will not proceed when the pH in the acidic solution is 1 or higher. Therefore, the alkaline additive composition containing an amine compound and the reaction products of glutaraldehyde and a hydrocarbon compound containing a hydroxyl group must come in contact with an acidic solution and become an acidic solution for a short period of time. Additive (A) of the present invention can be brought into contact with a sufficient quantity of acidic solution to maintain acidity, and after the additive reaction products are formed, be added to a tin or tin alloy plating solution, or additive (A) of the present invention can be directly added to an acidic tin or tin alloy plating solution.

The stannous ion that can be used with the present invention is a bivalent ion. Various types of compounds may be used if they are able to provide this type of ion in the plating bath. Examples include the stannous salt of inorganic acids such as sulfuric acid and hydrochloric acid, as well as organic acids such as methanesulfonic acid, citric acid, and malic acid, or the like. Preferable sources of stannous ions include, for example, the tin salt of an acid selected from the aforementioned organic acids. The tin salts of substituted or unsubstituted alkanesulfonic acid or alkanolsulfonic acid are more preferable, including compounds selected from the stannous salt of alkanesulfonic acids or alkanolsulfonic acids such as methanesulfonic acid, ethanesulfonic acid, propanesulfonic acid, 2-hydroxyethane-1-sulfonic acid, 2-hydroxypropane-1-sulfonic acid, or 1-hydroxypropane-2-sulfonic acid, and the like. Generally, the use of tin salts of organic acids that are used in commonly known plating solutions is preferable. These stannous ions may be used independently or as a mixture of two or more. The quantity of stannous ion in the plating solution is, for example, 10 g/L or more and 100 g/L or less, preferably 16 g/L or more and 70 g/L or less, and more preferably 20 g/L or more and 30 g/L or less of tin methanesulfate.

The acid component of the present invention can be either an inorganic acid or an organic acid. Examples of inorganic acids include sulfuric acid and hydrochloric acid, and the like. The organic acids can be an acid selected from an alkanesulfonic acid or an alkanolsulfonic acid. A preferable alkanesulfonic acid or alkanolsulfonic acid can be an acid which can be used with the aforementioned tin salts, and methanesulfonic acid is more preferable. These acid components may be used independently or as a mixture of two or more. The quantity of acid component in the plating bath solution is stoichiometrically equal to at least the same number of equivalents as bivalent tin ion present in the plating bath. For example, the quantity of free acid in the plating bath should be 15 mL/L or more and 500 mL/L or less, preferably 20 mL/L or more and 150 mL/L or less, and more preferably between 50 mL/L and 100 mL/L.

A surfactant may optionally be added to the plating solution of the present invention. The surfactant may be any type of surfactant, but nonionic surfactants are appropriate. Examples of preferable nonionic surfactants include polyoxyethylene lauryl ether, polyethylene glycol, polyoxyethylene alkyl ether, polyoxyethylene polyoxypropylene glycol, polyoxyethylene nonylphenyl ether, polyoxyethylene polyoxypropylene alkylamine, and polyoxyethylene adducts of ethylenediamines, and the like, but polyoxyethylene monoalkyl ether or phenolethoxylate are preferable. These surfactants can be commercially procured, and can be purchased from ADEKA Corporation as a product named Adekatol™ PC-8.

An appropriate concentration of surfactant in the plating bath, is for instance, 0.01 g/L or more and 50 g/L or less, preferably 0.05 g/L or more and 20 g/L or less, more preferably 0.1 g/L or more and 15 g/L or less.

Metal ions other than tin can optionally be added to the plating solution of the present invention. These metal ions include the ions of lead, tin, silver, bismuth, and thallium, and the like. Various types of compounds may be used if they are able to provide this type of ion in the plating bath. Examples include the lower valence metal salt of sulfuric acid, hydrochloric acid, and organic acids such as methane sulfonic acid, citric acid, and malic acid, or the like. These metal ions may be used independently or as a mixture of two or more.

The amount of metal ions other than tin in the plating solution, is for example, 0 g/L or more, and 30 g/L or less, preferably 0 g/L or more and 15 g/L or less.

An antioxidant may be arbitrarily used in the plating solution of the present invention. The antioxidant is used to prevent oxidation from bivalent tin to quadrivalent tin, and, for instance, hydroquinone, catechol, resorcin, phloroglucin, pyrogallol, hydroquinonesulfonic acid and salts thereof can be used. These antioxidants may be used independently or as a mixture of two or more.

An appropriate concentration of antioxidant in the plating bath is, for instance, 0.01 g/L or more and 10 g/L or less, preferably 0.1 g/L or more and 5.0 g/L or less, and more preferably 0.2 g/L or more and 2.0 g/L or less.

The tin electric plating solution of the present invention is adjusted to be in the acidic region. The pH of the plating bath is, for instance, less than 7, preferably 3 or lower, and more preferably 1 or lower. If necessary, commonly known additives such as pH adjusting agents, glossing agents, smoothing agents, conduction agents, anode dissolving agents, or the like, may also be added to the present invention.

The method of electroplating using the plating solution of the present invention may be a commonly known method. Methods such as barrel plating, through hole plating, rack plating, high-speed continuous plating, and the like, are compatible, and the concentration of each component in the plating solution may be selected arbitrarily. The electroplating method which uses the plating solution of the present invention may be performed at a plating bath temperature of between 10° C. and 65° C., preferably between room temperature and 50° C. Furthermore, the cathode current density is appropriately selected from a range of, for instance, 0.01 and 100 A/dm$^2$, preferably between 0.05 and 70 A/dm$^2$. During the plating process, the plating bath may be left unstirred, or a method such as stirring with a stirrer, or the like, or streaming, or the like, with a pump can be performed.

Embodiments of the present invention will be presented below, but the present invention is not restricted to these examples.

EMBODIMENT 1

The additive (A) of the present invention was prepared as shown below.

200 g of 1,2-propylene glycol (concentration 99%) was placed in a 1 L glass container and then 5 mL of methanesulfonic acid aqueous solution (concentration 70%) was added. The entire glass container was heated using a 50° C. water bath and the acidic propylene glycol solution was stirred until the temperature reached 40° C. While stirring the propylene glycol solution, 250 g of a 50% concentration glutaraldehyde aqueous solution was added and the solution was stirred for one hour while maintaining the temperature between 40° C. and 50° C. The solution that was clear became cloudy because of the addition of the glutaraldehyde aqueous solution. The solution that was obtained was cooled to 25° C., and then 240 g of a nonionic surfactant (product name: Adekatol™ PC-8 surfactant) was added while stirring the solution. The solution that was obtained was clear. The solution obtained was stirred for 5 minutes, and then 300 g of polyoxyethylenediamine compound (product name: JEFFAMINE™ XTJ-500) was added to the solution while stirring. The appearance of the solution was yellow and the temperature was 37° C. Stirring was continued until the appearance of the solution changed from a yellow to a clear brown color, and then 82 mL of deionized water was added and the solution was made to be 1 L. The solution that was obtained was cooled to room temperature (25° C.) by allowing to sit. Additive solution A with a brown appearance and a pH of 10.6 was obtained.

COMPARATIVE EXAMPLE 1

Reaction System when a Hydrocarbon Compound Containing a Hydroxyl Group is not Used 200 g of deionized water was placed in a 1 L glass container, and the entire container was heated using a 50° C. water bath, and then 250 g of a 50% concentration of glutaraldehyde was added while stirring. 240 g of a nonionic surfactant (product name: Adekatol™ PC-8 surfactant) was added while stirring the solution. The solution that was obtained was colorless and clear. The solution obtained was stirred for 5 minutes, and then 300 g of polyoxyethylenediamine compound (product name: JEFFAMINE™ XTJ-500) was added to the solution while stirring. The solution that was obtained was cooled to room temperature (25° C.) by allowing to sit. A brown gel similar to silicon rubber was obtained.

COMPARATIVE EXAMPLE 2

Additive solution B was obtained by the same method as Embodiment 1, except that 130 g of 85% concentration acetoaldehyde was added in place of the glutaraldehyde.

COMPARATIVE EXAMPLE 3

Additive solution C was obtained by the same method as Embodiment 1, except that 186 g of a 97% concentration butylaldehyde was added in place of the glutaraldehyde.

COMPARATIVE EXAMPLE 4

Additive solution D was obtained by the same method as Embodiment 1, except that 274 g of a 97% concentration benzaldehyde was added in place of the glutaraldehyde.

COMPARATIVE EXAMPLE 5

Additive solution E was obtained by the same method as Embodiment 1, except that 350 g of a 97% concentration anisaldehyde was added in place of the glutaraldehyde.

EMBODIMENT 2

Additive solution F was obtained by the same method as Embodiment 1, except that 245 g of ethanol (99.5% concentration) was added in place of the 1,2-propylene glycol.

EMBODIMENT 3

Additive solution G was obtained by the same method as Embodiment 1, except that 162 g of glycerin (99% concentration) was added in place of the 1,2-propylene glycol.

EMBODIMENT 4

Additive solution H was obtained by the same method as Embodiment 1, except that 360 g of glucose (98% concentration) was added in place of the 1,2-propylene glycol.

EMBODIMENT 5

Additive solution I was obtained by the same method as Embodiment 1, except that 367 g of sorbitol (97% concentration) was added in place of the 1,2-propylene glycol.

EMBODIMENT 6

Additive solution J was obtained by the same method as Embodiment 1, except that 164 g of ethylene glycol (99% concentration) was added in place of the 1,2-propylene glycol.

Adhesion Ratio Test

A tin plating solution was made from the following composition.

TABLE 1

| | |
|---|---|
| Stannous methanesulfonate | 31.2 g/L (12 g/L as tin) |
| methanesulfonic acid | 71 g/L |
| catechol | 0.5 g/L |
| Additive solution shown in Table 1 | 10 mL/L |
| Deionized water | remainder |
| pH | <1 |

Using the tin plating solution that was obtained, barrel plating was performed on the electrode region of resistors which are chip components at a temperature of 20° C. for 90 minutes at 0.1 A/dm$^2$. The electrode region of the chips had previously been coated with a 5 μm thick nickel film using nickel electroplating, water washed, and then the aforementioned tin plating was performed. The chip components which had been nickel plated were acid washed for five minutes using a 5% concentration of methanesulfonic acid aqueous solution (solution temperature 40° C.), water washed, neutralized by immersing for five minutes in a trisodium phosphate aqueous solution (50 g/L) at a solution temperature of 50° C., again water washed, and then dried.

The mutual adhesion of the chip components obtained was evaluated as the adhering rate based on the ratio of chip components which had adhered together from the total number of chip components. The aforementioned plating solution was made immediately after preparing the additive, three days after preparing the additive, and after allowing the additive to sit for one week after preparation, and the evaluation results are shown in Table 2. It is thought that the additive reaction product which is the active ingredient had decomposed in those samples where the adhering rate exceeded 20%, and subsequent evaluation was not performed. The appearance of the tin plating film that was obtained was also evaluated. The results are shown in Table 2. In all cases a uniform and semiglossy appearance was obtained.

TABLE 2

| | Additive | Immediately after preparation | 3 days after preparation | One week after preparation | Appearance |
|---|---|---|---|---|---|
| A | Embodiment 1 | 1% or less | 1% or less | 1% or less | Uniform, semiglossy |
| F | Embodiment 2 | 1% or less | 20% or more | Not measured | Uniform, semiglossy |
| G | Embodiment 3 | 1% or less | 20% or more | Not measured | Uniform, semiglossy |
| H | Embodiment 4 | 1% or less | 20% or more | Not measured | Uniform, semiglossy |
| I | Embodiment 5 | 1% or less | 20% or more | Not measured | Uniform, semiglossy |
| J | Embodiment 6 | 1% or less | 1% or less | 1% or less | Uniform, semiglossy |
| NONE | Comparative Example 1 | 20% or more | Not measured | Not measured | Uniform, semiglossy |
| B | Comparative Example 2 | 20% or more | Not measured | Not measured | Uniform, semiglossy |
| C | Comparative Example 3 | 20% or more | Not measured | Not measured | Uniform, semiglossy |
| D | Comparative Example 4 | 20% or more | Not measured | Not measured | Uniform, semiglossy |
| E | Comparative Example 5 | 20% or more | Not measured | Not measured | Uniform, semiglossy |

From the above results, it was determined that significantly superior results could be obtained by using glutaraldehyde as compared to other aldehydes. Furthermore, with regards to the alcohol that reacts with the glutaraldehyde, an effect was observed even when a monoalcohol or glycerin was used, but the effect was maintained for a significantly longer period of time by using a glycol.

COMPARATIVE EXAMPLE 6

3.2 g of the reaction products of glutaraldehyde and 1,2-propylene glycol prepared for Embodiment 1, 2.4 g of nonionic surfactant (product name: Adekatol™ PC-8 surfactant) and 3 g of a polyoxyethylenediamine compound (product name: JEFFAMINE™ XTJ-500) were individually added as the additive to a tin plating solution containing 31.2 g/L of stannous methanesulfonate, 71 g/L of methanesulfonic acid, and 0.5 g/L of catechol, and the adhering ratio was evaluated as shown above. The results show that the adhering ratio immediately after preparation was 20% or more, and there was no improvement observed in the adhering rate.

COMPARATIVE EXAMPLE 7

Using the same method as the aforementioned adhering rate test, glutaraldehyde, 1,2-propylene glycol, nonionic surfactant (product name: Adekatol™ PC-8 surfactant) and polyoxyethylenediamine compound (product name: JEFFAMINE™ XTJ-500) at essentially the same ratio as was included in the additive solution of Embodiment 1 to make a total of 10 g were individually added to a tin plating solution in place of the additive solution, and the adhering rate was evaluated. The results show that the adhering ratio was 20% or more and there was no improvement observed in the adhering rate.

EMBODIMENT 7

Solderability Test

2 L of a tin plating solution that contains the additive of Embodiment 1 was prepared, and tin plating was performed for 90 minutes at 0.1 A/dm2 while stirring using a barrel at a solution temperature of 20° C. on chip components that had a nickel plating film on the electrode region. The tin plating film obtained was subjected to a humidity resistance test at 105° C., 100% humidity, for 4 hours (PCT treatment 105° C., relative humidity 100%, 4 hours), and the solderability of the tin plating film after the humidity resistance test was determined by measuring and evaluating the zero cross time by the meniscograph method using a solder checker. The measurement conditions were as shown below. The solderability obtained at the following measurement conditions was 2.5 seconds.

TABLE 3

| Zero cross time measurement conditions | |
|---|---|
| Tester: | Multi-Solderability Tester SWET-2100 (manufactured by Tarutin Kester) |
| Measurement mode: | Paste Quick Mode |
| Solder paste: | Sn/Ag/Bi/Cu = 96.0/0.5/1.0/0.5 |
| Bath temperature: | 245° C. |
| Immersion depth: | 0.25 mm |
| Immersion speed: | 2.0 mm/second |
| Retention time: | 10 seconds |
| Afterheat: | 8 seconds |

What is claimed is:
1. A tin electroplating solution comprising:
   (1) stannous ions;
   (2) a reaction product obtained by reacting glutaraldehyde and at least one compound selected from hydrocarbon compounds containing a hydroxyl group in the presence of an acid; and
   (3) at least one amine compound.
2. The tin or tin alloy electroplating solution of claim 1, further comprising a nonionic surfactant.
3. The tin electroplating solution of claim 1, further comprising a tin antioxidant.
4. The tin electroplating solution of claim 1, further comprising one or more metals selected from the group consisting of lead, silver, bismuth and thallium.

* * * * *